(12) United States Patent
Letts et al.

(10) Patent No.: US 7,589,124 B2
(45) Date of Patent: Sep. 15, 2009

(54) NITROSATED AND/OR NITROSYLATED CYCLOOXYGENASE-2 SELECTIVE INHIBITORS, COMPOSITIONS AND METHODS OF USE

(75) Inventors: L. Gordon Letts, Dover, MA (US); David S. Garvey, Dover, MA (US)

(73) Assignee: NicOx, S.A. (FR)

( * ) Notice: Subject to any disclaimer, the term of this patent is extended or adjusted under 35 U.S.C. 154(b) by 0 days.

(21) Appl. No.: 11/730,886

(22) Filed: Apr. 4, 2007

(65) Prior Publication Data
US 2007/0179195 A1    Aug. 2, 2007

Related U.S. Application Data

(62) Division of application No. 10/718,060, filed on Jun. 10, 2003, now Pat. No. 7,220,749.

(60) Provisional application No. 60/387,433, filed on Jun. 11, 2002.

(51) Int. Cl.
A61K 31/34 (2006.01)
C07C 229/42 (2006.01)

(52) U.S. Cl. .................. 514/539; 560/49

(58) Field of Classification Search ........... 514/539; 560/49
See application file for complete search history.

(56) References Cited

U.S. PATENT DOCUMENTS

| | | | |
|---|---|---|---|
| 5,593,339 A | 1/1997 | Yam et al. |
| 5,621,000 A | 4/1997 | Arena et al. |
| 5,700,947 A | 12/1997 | Soldato et al. |
| 5,703,073 A | 12/1997 | Garvey et al. |
| 5,780,495 A | 7/1998 | Del Soldato et al. |
| 5,844,696 A | 12/1998 | Massie et al. |
| 5,861,426 A | 1/1999 | Del Soldato et al. |
| 6,040,341 A | 3/2000 | Del Soldato et al. |
| 6,043,233 A | 3/2000 | Garvey et al. |
| 6,046,191 A | 4/2000 | Hamley et al. |
| 6,048,858 A | 4/2000 | Garvey et al. |
| 6,051,588 A | 4/2000 | Garvey et al. |
| 6,057,347 A | 5/2000 | Garvey et al. |
| 6,083,515 A | 7/2000 | Garvey et al. |
| 6,143,734 A | 11/2000 | Garvey et al. |
| 6,242,432 B1 | 6/2001 | del Soldato et al. |
| 6,248,745 B1 | 6/2001 | Hamley et al. |
| 6,291,523 B1 | 9/2001 | Fujimoto et al. |
| 6,297,260 B1 | 10/2001 | Bandarage et al. |
| 6,323,234 B1 | 11/2001 | Garvey et al. |
| 6,355,680 B1 | 3/2002 | Cohen |
| 6,369,260 B1 | 4/2002 | Sannicolo' et al. |
| 6,410,791 B1 | 6/2002 | Soldato et al. |
| 6,482,846 B1 | 11/2002 | Garvey et al. |
| 6,512,137 B1 | 1/2003 | Del Soldato et al. |
| 6,573,252 B1 | 6/2003 | Del Soldato et al. |
| 6,593,339 B1 | 7/2003 | Eek et al. |
| 6,593,347 B2 | 7/2003 | Bandarage et al. |
| 6,613,784 B1 | 9/2003 | Benedini et al. |

FOREIGN PATENT DOCUMENTS

| | | |
|---|---|---|
| EP | 0 904 110 | 3/1999 |
| WO | WO-94/04484 | 3/1994 |
| WO | WO-94/12463 | 6/1994 |
| WO | WO-95/09831 | 4/1995 |
| WO | WO-95/30641 | 11/1995 |
| WO | WO-96/32946 | 10/1996 |
| WO | WO-97/16405 | 5/1997 |
| WO | WO-97/31654 | 9/1997 |
| WO | WO-98/09948 | 3/1998 |
| WO | WO-99/11605 | 3/1999 |
| WO | WO-99/44595 | 9/1999 |
| WO | WO-99/45004 | 9/1999 |
| WO | WO-00/00200 | 1/2000 |
| WO | WO-00/06585 | 2/2000 |
| WO | WO-00/25776 | 5/2000 |
| WO | WO-00/44705 | 8/2000 |
| WO | WO-00/51988 | 9/2000 |
| WO | WO-00/61537 | 10/2000 |
| WO | WO-00/61541 | 10/2000 |

(Continued)

OTHER PUBLICATIONS

Science (1999), vol. 286, 531-537.*
Cancer and Metastasis Reviews (1998), 17(1), 91-106.*
International Search Report from PCT/US03/18052, Dec. 15, 2003.
Barrachina, et al., Eur. J. Pharmacol., 281: R3-R4 (1995).
Boughton-Smith, et al., Eur. J. Pharmacol., 191:485-488 (1990).
Brown, et al., Eur. J. Pharmacol., 103-104 (1992).
Carty, et al., Agents Actions, 39:157-165 (1993).
Conforti, et al., Agents Action, 40(3): 176-180 (1993).

(Continued)

Primary Examiner—Rebecca L Anderson
(74) Attorney, Agent, or Firm—Wilmer Cutler Pickering Hale and Dorr LLP

(57) ABSTRACT

The invention provides novel nitrosated and/or nitrosylated cyclooxygenase 2 (COX-2) selective inhibitors and novel compositions and kits comprising at least one nitrosated and/or nitrosylated cyclooxygenase 2 (COX-2) selective inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or, optionally, at least one therapeutic agent. The invention also provides methods for treating inflammation, pain and fever; for treating and/or improving the gastrointestinal properties of COX-2 selective inhibitors; for facilitating wound healing; for treating and/or preventing renal and/or respiratory toxicity; for treating and/or preventing other disorders resulting from elevated levels of cyclooxygenase-2; and for improving the cardiovascular profile of COX-2 selective inhibitors.

19 Claims, No Drawings

FOREIGN PATENT DOCUMENTS

| | | |
|---|---|---|
| WO | WO-00/61549 | 10/2000 |
| WO | WO-00/61604 | 10/2000 |
| WO | WO-00/72838 | 12/2000 |
| WO | WO-01/00563 | 1/2001 |
| WO | WO-01/04082 | 1/2001 |
| WO | WO-01/10814 | 2/2001 |
| WO | WO-01/12584 | 2/2001 |
| WO | WO-01/23346 | 4/2001 |
| WO | WO-01/45703 | 6/2001 |
| WO | WO-01/56555 | 8/2001 |
| WO | WO-01/87343 | 11/2001 |
| WO | WO-01/93680 | 12/2001 |
| WO | WO-02/11706 | 2/2002 |
| WO | WO-02/11707 | 2/2002 |
| WO | WO-02/20090 | 3/2002 |
| WO | WO-02/30866 | 4/2002 |
| WO | WO-02/051385 | 7/2002 |
| WO | WO-02/053188 | 7/2002 |
| WO | WO-02/092072 | 11/2002 |
| WO | WO-02/100400 | 12/2002 |
| WO | WO-03/000642 | 1/2003 |
| WO | WO-03/000643 | 1/2003 |
| WO | WO-03/013499 | 2/2003 |
| WO | WO-03/033001 | 4/2003 |
| WO | WO-03/049720 | 6/2003 |
| WO | WO-03/084550 | 10/2003 |
| WO | WO-03/094924 | 11/2003 |
| WO | WO-2004/000273 | 12/2003 |
| WO | WO-2004/000300 | 12/2003 |
| WO | WO-2004/000781 | 12/2003 |

OTHER PUBLICATIONS

Cuzzolin, et al., Pharmacol. Res. 29(1):89-97 (1994).
Cuzzolin, et al., Pharmacol. Res. 31:61-65 (1995).
Del Soldato, et al., Br. J. Pharmacol., 67:33-37 (1979).
Elliott, et al., Gastroenterol., 109:524-530 (1995).
Kitigawa, et al., J. Pharmacol. Exp. Therp., 253:1133-1137 (1990).
Konturek, et al., Eur. J. Pharmacol., 239:215-217 (1993).
Langford, et al., Arterioscler, Thromb. Vasc. Biol. 16:51-57 (1996).
MacNaughton, et al., Life Sciences, 45:1869-1876 (1989).
Palmer, et al., Nature, 333:664-444 (1998).
Rachmilewitz, et al., Gut, 35:1394-1397 (1994).
Reuter, et al., Life Sciences, 55(1):1-8 (1994).
Reuter, et al., Gastroenterol., 106(4), A759 (1994).
Wallace, et al., Trends Pharmacol., Sci., 15(11):405-406 (1994).
Wallace, et al., J. Gastroenterol. Hepatol., 9:S40-S44 (1994).
Wallace, et al., Novel Molecular Approaches to Anti-Inflammatory Theory, 121-129 (1994).
Wallace, et al., Gastroenterol., 106(4), Part 2, A208 (1994) Abstract.
Wallace, et al., Eur. J. Pharmacol., 257:249-255 (1994).
Wallace, et al., Gastroenterol., 107:173-179 (1994).
Wallace, et al., J. Clin. Invest., 96:2711-2718 (1995).
Wallace, et al., Expert Opinion Investigational Drugs, 4(7):613-619 (1995).
Wallace, et al., Eur. J. Pharmacol., 63-68 (1995).
Williams, et al., Cancer Research, 63:3285-3289 (Apr. 15, 2001).
Young, Delano V. et al., A comparison of the cyclooxygenase inhibitor-NO donors (CINOD), NMI-1182 and AZD3582, using in vitro biochemical and pharmacological methods, Biochemical Pharmacology, 70, pp. 1343-1351 (2005).

* cited by examiner

NITROSATED AND/OR NITROSYLATED CYCLOOXYGENASE-2 SELECTIVE INHIBITORS, COMPOSITIONS AND METHODS OF USE

RELATED APPLICATIONS

This application is a divisional of U.S. application Ser. No. 10/718,060, filed Jun. 10, 2003, issued as U.S. Pat. No. 7,220, 749, which claims priority under 35 USC §119 to U.S. Provisional Application No. 60/387,433 filed Jun. 11, 2002.

FIELD OF THE INVENTION

The invention describes novel nitrosated and/or nitrosylated cyclooxygenase 2 (COX-2) selective inhibitors and novel compositions comprising at least one nitrosated and/or nitrosylated cyclooxygenase 2 (COX-2) selective inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel compositions comprising at least one COX-2 selective inhibitor, that is optionally nitrosated and/or nitrosylated, and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The invention also provides novel kits comprising at least one COX-2 selective inhibitor, that is optionally nitrosated and/or nitrosylated, and, optionally, at least one nitric oxide donor and/or at least one therapeutic agent. The invention also provides methods for treating inflammation, pain and fever; for treating and/or improving the gastrointestinal properties of COX-2 selective inhibitors; for facilitating wound healing; for treating and/or preventing renal and/or respiratory toxicities; for treating and/or preventing other disorders resulting from elevated levels of cyclooxygenase-2; and for improving the cardiovascular profile of COX-2 selective inhibitors. The novel nitrosated cyclooxygenase 2 selective inhibitors of the invention are preferably nitrosated derivatives of 2(2-((2-chloro-6-fluorophenyl)amino)5-methylphenyl)acetic acid.

BACKGROUND OF THE INVENTION

Nonsteroidal anti-inflammatory compounds (NSAIDs) are widely used for the treatment of pain, inflammation, and acute and chronic inflammatory disorders such as osteoarthritis and rheumatoid arthritis. These compounds inhibit the activity of the enzyme cyclooxygenase (COX), also known as prostaglandin G/H synthase, which is the enzyme that converts arachidonic acid into prostanoids. The NSAIDs also inhibit the production of other prostaglandins, especially prostaglandin $G_2$, prostaglandin $H_2$ and prostaglandin $E_2$, thereby reducing the prostaglandin-induced pain and swelling associated with the inflammation process. The chronic use of NSAIDs has been associated with adverse effects, such as gastrointestinal ulceration and renal toxicity. The undesirable side effects are also due to the inhibition of prostaglandin in the affected organ.

Recently two isoforms of cyclooxygenase, encoded by two distinct genes (Kujubu et al, *J. Biol. Chem.*, 266, 12866-12872 (1991)), have been identified—a constitutive form, cyclooxygenase-1 (COX-1), and an inductive form, cyclooxygenase-2 (COX-2). It is thought that the antiinflammatory effects of NSAIDs are mediated by the inhibition of COX-2, whereas the side effects seem to be caused by the inhibition of COX-1. The NSAIDs currently on the market either inhibit both isoforms of COX with little selectivity for either isoform or are COX-1 selective. Recently compounds that are COX-2 selective inhibitors have been developed and marketed. These COX-2 selective inhibitors have the desired therapeutic profile of an antiinflammatory drug without the adverse effects commonly associated with the inhibition of COX-1. However, these compounds can result in dyspepsia and can cause gastropathy (Mohammed et al, *N. Engl. J. Med.*, 340(25) 2005 (1999)). Additionally the COX-2 selective inhibitors can increase the risk of cardiovascular events in a patient (Mukherjee et al., *JAMA* 286(8) 954-959 (2001)); Hennan et al., Circulation, 104:820-825 (2001)).

There is still a need in the art for novel COX-2 selective inhibitor compounds that have gastroprotective properties, facilitate wound healing, decreased renal and/or respiratory toxicity and dyspepsia, improved cardiovascular profile and that can be used at low dosages. The invention is directed to these, as well as other, important ends.

SUMMARY OF THE INVENTION

The invention provides novel nitrosated and/or nitrosylated derivatives of COX-2 selective inhibitors, or a pharmaceutically acceptable salt thereof. These compounds are potent analgesics, have antiinflammatory properties and have an unexpected potential for facilitating wound healing. The novel compounds also have unexpected properties in the treatment and/or prevention of renal and/or respiratory toxicity and for improving the cardiovascular profile of COX-2 selective inhibitors. The COX-2 selective inhibitor, or a pharmaceutically acceptable salt thereof, can be nitrosated and/or nitrosylated through one or more sites, such as oxygen (hydroxyl condensation), sulfur (sulfhydryl condensation) and/or nitrogen. The invention also provides compositions comprising the novel compounds described herein in a pharmaceutically acceptable carrier.

The invention is also based on the discovery that administering at least one parent COX-2 selective inhibitor, and, optionally, at least one nitric oxide donor reduces the gastrointestinal distress induced by COX-2 selective inhibitors. Nitric oxide donors include, for example, S-nitrosothiols, nitrites, nitrates, N-oxo-N-nitrosamines, SPM 3672, SPM 5185, SPM 5186 and analogues thereof, and substrates of the various isozymes of nitric oxide synthase. Thus, another aspect of the invention provides compositions comprising at least one parent COX-2 selective inhibitor and at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The invention also provides for such compositions in a pharmaceutically acceptable carrier.

Yet another aspect of the invention provides compositions comprising at least one COX-2 selective inhibitor, that is optionally substituted with at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase, and/or, optionally, at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. The invention also provides for such compositions in a pharmaceutically acceptable carrier.

Yet another aspect of the present invention provides methods for treating and/or preventing inflammation, pain and fever; for treating and/or improving gastrointestinal properties of COX-2 inhibitors; for facilitating wound healing; for treating and/or preventing renal and/or respiratory toxicity; and for treating and/or preventing COX-2 mediated disorders (i.e., disorders resulting from elevated levels of COX-2) in a patient in need thereof which comprises administering to the patient a therapeutically effective amount of at least one COX-2 selective inhibitor, that is optionally substituted with at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e., NO donors). The methods can optionally further comprise the administration of at least one therapeutic agent, such as, for example, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. In this aspect of the invention, the methods can involve administering the COX-2 selective inhibitors, that are optionally nitrosated and/or nitrosyalted, administering the COX-2 selective inhibitors, that are optionally nitrosated and/or nitrosylated and NO donors, administering the COX-2 selective inhibitors, that are optionally nitrosated and/or nitrosylated, and therapeutic agents, or administering the COX-2 selective inhibitors, that are optionally nitrosated and/or nitrosylated, NO donors and therapeutic agents. The selective COX-2 inhibitors, nitric oxide donors, and/or therapeutic agents can be administered separately or as components of the same composition in one or more pharmaceutically acceptable carriers.

Yet another aspect of the invention provides methods for improving the cardiovascular profile of COX-2 selective inhibitors in a patient in need thereof which comprises administering to the patient a therapeutically effective amount of at least one COX-2 selective inhibitor, optionally substituted with at least one $NO_2$ and/or NO group (i.e. nitrosated and/or nitrosylated), and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e. NO donor). The methods can optionally further comprise the administration of at least one of 3-hydroxy-3-methylglutaryl coenzyme A (HMG-CoA) inhibitors, antiplatelet agents, thrombin inhibitors, thromboxane inhibitors, and mixtures of two or more thereof. In this aspect of the invention, the methods can involve administering the nitrosated and/or nitrosylated COX-2 selective inhibitors, administering the COX-2 selective inhibitors, that are optionally nitrosated and/or nitrosylated, and NO donors, administering the COX-2 selective inhibitors, that are optionally nitrosated and/or nitrosylated, and at least one of 3-hydroxy-3-methylglutaryl coenzyme A (HMG-CoA) inhibitors, antiplatelet agents, thrombin inhibitors or thromboxane inhibitors, or administering the COX-2 selective inhibitors, that are optionally nitrosated and/or nitrosylated, NO donors, and at least one of 3-hydroxy-3-methylglutaryl coenzyme A (HMG-CoA) inhibitors, antiplatelet agents, thrombin inhibitors or thromboxane inhibitors. The COX-2 inhibitors, nitric oxide donors, and/or 3-hydroxy-3-methylglutaryl coenzyme A (HMG-CoA) inhibitors, antiplatelet agents, thrombin inhibitors or thromboxane inhibitors can be administered separately or as components of the same composition in one or more pharmaceutically acceptable carriers.

In yet another aspect the invention provides kits comprising at least one COX-2 selective inhibitor, that is optionally substituted at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The kit can further comprise at least one therapeutic agent, such as, for example, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. The COX-2 selective inhibitor, the nitric oxide donor and/or therapeutic agent, can be separate components in the kit or can be in the form of a composition in one or more pharmaceutically acceptable carriers.

DETAILED DESCRIPTION OF THE INVENTION

As used throughout the disclosure, the following terms, unless otherwise indicated, shall be understood to have the following meanings.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 µM and a cyclooxygenase-1 $IC_{50}$ of greater than about 5 µM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 µM, and preferably of greater than 20 µM. The compound can also inhibit the enzyme, lipoxygenase. Such selectivity may indicate an ability to reduce the incidence of common NSAID-induced side effects.

"Parent COX-2 inhibitor" refers to a non-nitrosated and/or non-nitrosylated COX-2 inhibitor, or pharmaceutically acceptable salts thereof or pharmaceutically acceptable esters thereof. "Parent COX-2 inhibitor" includes the compounds of Formula (I) before they are nitrosated and/or nitrosylated by the methods described herein.

"Therapeutic agent" includes any therapeutic agent that can be used to treat or prevent the diseases described herein. "Therapeutic agents" include, for example, steroids, nonsteroidal antiinflammatory compounds, 5-lipoxygenase inhibitors, leukotriene $B_4$ receptor antagonists, leukotriene $A_4$ hydrolase inhibitors, 3-hydroxy-3-methylglutaryl coenzyme A inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. Therapeutic agent includes the pro-drugs and pharmaceutical derivatives thereof including but not limited to the corresponding nitrosated and/or nitrosylated derivatives. Although nitric oxide donors have therapeutic activity, the term "therapeutic agent" does not include the nitric oxide donors described herein, since nitric oxide donors are separately defined.

"Cardiovascular disease or disorder" refers to any cardiovascular disease or disorder known in the art, including, but not limited to, restenosis, atherosclerosis, atherogenesis, angina, (particularly chronic, stable angina pectoris), ischemic disease, congestive heart failure or pulmonary edema associated with acute myocardial infarction, thrombosis, controlling blood pressure in hypertension (especially hypertension associated with cardiovascular surgical procedures), thromboemboembolic events, platelet aggregation, platelet adhesion, smooth muscle cell proliferation, vascular complications associated with the use of medical devices, wounds associated with the use of medical devices, cerebrovascular ischemic events, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, ischemic stroke, transient ischemic stroke, thromboemboembolic events, pulmonary thromboembolism, cerebral thromboembolism, thrombophlebitis, thrombocytopenia, bleeding disorders and/or any other complications which occur either directly or indirectly as a result of the foregoing disorders.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. Restenosis can also occur following a number of invasive surgical techniques, such as, for example, transplant surgery, vein grafting, coronary artery bypass surgery, endarterectomy, heart transplantation, balloon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery. Atherosclerotic cardiovascular disease, coronary heart disease (also known as coronary artery disease or ischemic heart disease), cerebrovascular disease and peripheral vessel disease are all common manifestations of atherosclerosis and are therefore encompassed by the terms "atherosclerosis" and "atherosclerotic disease".

"Improving the cardiovascular profile" refers to and includes reducing the risk of thromboembolic events, reducing the risk of developing atherosclerosis and atherosclerotic diseases, and inhibiting platelet aggregation of the parent COX-2 inhibitor.

"Thromboemboembolic events" includes, but is not limited to, ischemic stroke, transient ischemic stroke, myocardial infarction, angina pectoris, thrombosis, thromboembolism, thrombotic occlusion and reocclusion, acute vascular events, restenosis, transient ischemic attacks, and first and subsequent thrombotic stroke. Patients who are at risk of developing thromboembolic events, may include those with a familial history of, or genetically predisposed to, thromboembolic disorders, who have had ischemic stroke, transient ischemic stroke, myocardial infarction, and those with unstable angina pectoris or chronic stable angina pectoris and patients with altered prostacyclin/thromboxane $A_2$ homeostasis or higher than normal thromboxane $A_2$ levels leading to increase risk for thromboembolism, including patients with diabetes and rheumatoid arthritis.

"Thromboxane inhibitor" refers to any compound that reversibly or irreversibly inhibits thromboxane synthesis, and includes compounds which are the so-called thromboxane $A_2$ receptor antagonists, thromboxane $A_2$ antagonists, thromboxane $A_2$/prostaglandin endoperoxide antagonists, thromboxane receptor (TP) antagonists, thromboxane antagonists, thromboxane synthase inhibitors, and dual acting thromboxane synthase inhibitors and thromboxane receptor antagonists. The characteristics of the preferred thromboxane inhibitor should include the suppression of thromboxane $A_2$ formation (thromboxane synthase inhibitors) and/or blockade of thromboxane $A_2$ and prostaglandin $H_2$ platelet and vessel wall (thromboxane receptor antagonists). The effects should block platelet activation and therefore platelet function.

"Thromboxane $A_2$ receptor antagonist" refers to any compound that reversibly or irreversibly blocks the activation of any thromboxane $A_2$ receptor.

"Thromboxane synthase inhibitor" refers to any compound that reversibly or irreversibly inhibits the enzyme thromboxane synthesis thereby reducing the formation of thromboxane $A_2$. Thromboxane synthase inhibitors may also increase the synthesis of antiaggregatory prostaglandins including prostacyclin and prostaglandin $D_2$. Thromboxane $A_2$ receptor antagonists and thromboxane synthase inhibitors and can be identified using the assays described in Tai, Methods of Enzymology, Vol. 86, 110-113 (1982); Hall, *Medicinal Research Reviews,* 11:503-579 (1991) and Coleman et al., *Pharmacol*

Rev., 46: 205-229 (1994) and references therein, the disclosures of which are incorporated herein by reference in its entirety.

"Dual acting thromboxane receptor antagonist and thromboxane synthase inhibitor" refers to any compound that simultaneously acts as a thromboxane $A_2$ receptor antagonist and a thromboxane synthase inhibitor.

"Thrombin inhibitors" refers to and includes compounds that inhibit hydrolytic activity of thrombin, including the catalytic conversion of fibrinogen to fibrin, activation of Factor V to Va, Factor VIII to VIIIa, Factor XIII to XIIIa and platelet activation. Thrombin inhibitors may be identified using assays described in Lewis et at., Thrombosis Research. 70: 173-190 (1993):

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

"Platelet activation" refers either to the change in conformation (shape) of a cell, expression of cell surface proteins (e.g., the IIb/IIIa receptor complex, loss of GPIb surface protein), and secretion of platelet derived factors (e.g., serotonin, growth factors).

"Patient" refers to animals, preferably mammals, most preferably humans, and includes males and females, and children and adults.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO−, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamido and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon triple bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxo" refers to =O.

"Oxy" refers to —O$^-$R$_{77}^+$ wherein $R_{77}$ is an organic or inorganic cation.

"Oxime" refers to (=N—OR$_{81}$) wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone refers to (=N—N($R_{81}$)($R'_{81}$)) wherein $R'_{81}$ is independently selected from $R_{81}$, and $R_{81}$ is as defined herein.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}$NH—, wherein $R_{50}$ is an alkyl group, as defined herein. Exemplary alkylamino groups include methylamino, ethylamino, butylamino, cyclohexylamino, and the like.

"Arylamino" refers to $R_{55}$NH—, wherein $R_{55}$ is an aryl group, as defined herein.

"Dialkylamino" refers to $R_{52}R_{53}$N—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}$N—, wherein $R_{55}$ and $R_{60}$ are each independently an aryl group, as defined herein.

"Alkylarylamino or arylalkylamino" refers to $R_{52}R_{55}$N—, wherein $R_{52}$ is an alkyl group, as defined herein, and $R_{55}$ is an aryl group, as defined herein.

"Alkylarylalkylamino" refers to $R_{52}R_{79}$N—, wherein $R_{52}$ is an alkyl group, as defined herein, and $R_{79}$ is an arylalkyl group, as defined herein.

"Alkylcycloalkylamino" refers to $R_{52}R_{80}$N—, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —$S(O)_2$—.

"Sulfonic acid" refers to —$S(O)_2OR_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein.

"Sulfonic ester" refers to —$S(O)_2OR_{58}$, wherein $R_{58}$ is an alkyl group, an aryl group, or an aryl heterocyclic ring, as defined herein.

"Sulfonamido" refers to —$S(O)_2$—N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}$S—, wherein $R_{50}$ is an alkyl group, as defined herein (preferably a lower alkyl group, as defined herein).

"Arylthio" refers to $R_{55}$S—, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—$S(O)_2$—, wherein $R_{50}$ is an alkyl group, as defined herein.

"Alkylsulfonyloxy" refers to $R_{50}$—$S(O)_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—$S(O)_2$—, wherein $R_{55}$ is an aryl group, as defined herein.

"Arylsulfonyloxy" refers to $R_{55}$—$S(O)_2$—O—, wherein $R_{55}$ is an aryl group, as defined herein.

"Amidyl" refers to $R_{51}$C(O)N($R_{57}$)— wherein $R_{51}$ and $R_{57}$ are each independently a hydrogen atom, an alkyl group, an aryl group or an arylheterocyclic ring, as defined herein.

"Ester" refers to $R_{51}$C(O)O— wherein $R_{51}$ is a hydrogen atom, an alkyl group, an aryl group or an arylheterocyclic ring, as defined herein.

"Carbamoyl" refers to —O—C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)$OR_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)$OR_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

Compounds that donate, transfer or release nitric oxide species in vivo have been recognized as having a wide spectrum of advantages and applications. The invention is based on the unexpected discovery of the effects of such compounds alone and together with one or more COX-2 inhibitors. Treatment or prevention of inflammation, pain and fever; treatment and/or improvement of the gastrointestinal properties of COX-2 inhibitors; facilitation of wound healing; and treatment and/or prevention of renal and/or respiratory toxicity and cyclooxygenase-2 mediated disorders can be obtained by the use of COX-2 inhibitors of the invention; or by the use of COX-2 inhibitors in conjunction with one or more compounds that donate, release or transfer nitric oxide and/or stimulate endogenous production of NO and/or EDRF in vivo and/or is a substrate for nitric oxide synthase, and, optionally, with one or more therapeutic agents.

The COX-2 selective inhibitors, that are optionally nitrosated and/or nitrosylated, can be used alone or in conjunction with one or more compounds that donate, release or transfer nitric oxide and/or stimulate endogenous production of NO and/or EDRF in vivo and/or is a substrate for nitric oxide synthase, and/or with one or more therapeutic agents, such as for example, steroids, nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, analgesics, *Helicobacter pylori* inhibitors, proton pump inhibitors, isoprostane inhibitors, and mixtures of two or more thereof. These novel compounds and novel compositions of the present invention are described in more detail herein.

In one embodiment, the invention described compounds of Formula (I), and pharmaceutically acceptable salts thereof;

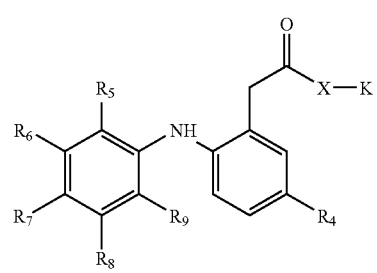

(I)

wherein:
$R_4$ is methyl or ethyl;
$R_5$ is chloro or fluoro;
$R_6$ is hydrogen or fluoro;
$R_7$ is hydrogen, fluoro, chloro, methyl, ethyl, methoxy, ethoxy or hydroxyl;
$R_8$ is hydrogen or fluoro;
$R_9$ is chloro, fluoro, triflurormethyl or methyl;
X is an oxygen, —S(O)$_n$— or —N($R_a$)$R_i$—;
K is:
  a) —$W_a$—$E_b$—(C($R_e$)($R_f$))$_p$—$E_c$—(C($R_e$)($R_f$))$_x$—$W_d$—(C($R_e$)($R_f$))$_y$—$W_i$—$E_j$—$W_g$—(C($R_e$)($R_f$))$_z$—T—Q; or
  b) —$W_a$—$E_b$—(C($R_e$)($R_f$))$_p$—$E_c$—(C($R_e$)($R_f$))$_x$—$W_d$—(C($R_e$)($R_f$))$_y$—$W_i$—$E_j$—$W_g$—(C($R_h$)($R_f$))$_z$—$R_3$ and with the proviso that at least one $R_e$ is selected as —T—Q, or —(C($R_g$)($R_h$))$_k$—T—Q when K is (b); and with the further proviso that "X—K" in the compounds of Formula (I), does not include nitroxyl lower alkyl esters such as 4-(nitroxyl) butyl 2(2-((2-chloro-6-fluorophenyl)amino)5-methylphenyl)acetate as disclosed in WO 99/11605;
$R_3$ is:

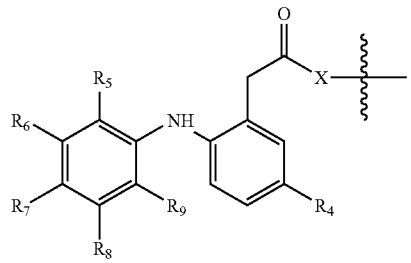

Q is —NO or —NO$_2$;
a, b, c, d, g, i and j are each independently an integer from 0 to 3;
p, x, y and z are each independently an integer from 0 to 10;
W at each occurrence is independently —C(O)—, —C(S)—, —T—, —(C($R_e$)($R_f$))$_h$—, an alkyl group, an aryl group, a heterocyclic ring, an arylheterocyclic ring, or —(CH$_2$CH$_2$O)$_q$—;
E at each occurrence is independently —T—, an alkyl group, an aryl group, —(C($R_e$)($R_f$))$_h$—, a heterocyclic ring, an arylheterocyclic ring, or —(CH$_2$CH$_2$O)$_q$—;
h is an integer form 1 to 10;
q is an integer from 1 to 5;
$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkyl-cycloalkyl, an alkylheterocyclic ring, a cycloalkylalkyl, a cycloalkylthio, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, a urea, a phosphoryl, a nitro, $W_h$, —T—Q, or —(C(R_g)(R_h))_k—T—Q, or $R_e$ and $R_f$ taken together with the carbons to which they are attached form a carbonyl, a methanthial, a heterocyclic ring, a cycloalkyl group, an aryl group, an oxime, a hydrazone or a bridged cycloalkyl group;

$R_g$ and $R_h$ at each occurrence are independently $R_e$;

k is an integer from 1 to 3;

T at each occurrence is independently a covalent bond, a carbonyl, an oxygen, —S(O)O— or —N($R_a$)$R_i$—;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —CH_2—C(T—Q)($R_e$)($R_f$), a bond to an adjacent atom creating a double bond to that atom, —(N_2O_2—)⁻.M⁺, wherein M⁺ is an organic or inorganic cation;

with the proviso that the nitrosated and/or nitrosylated compounds of Formula (I) must contain at least one —NO group or at least one —NO_2 group, and wherein the at least one —NO group or the at least one —NO_2 group is linked to the compounds of Formula (I) through an oxygen atom, a nitrogen atom or a sulfur atom.

In cases where $R_e$ and $R_f$ are a heterocyclic ring or $R_e$ and $R_f$ taken together with the carbon atoms to which they are attached are a heterocyclic ring, then $R_i$ can be a substituent on any disubstituted nitrogen contained within the radical where $R_i$ is as defined herein.

In cases where multiple designations of variables that are in sequence are selected as a "covalent bond" or the integer selected is 0, the intent is to denote a single covalent bond connecting one radical to another. For example, $E_0$ would denote a covalent bond, while $E_2$ denotes (E-E) and (C($R_e$)($R_f$))_2 denotes —C($R_e$)($R_f$)—C($R_e$)($R_f$)—.

In a preferred embodiment of the invention, the parent COX-2 selective inhibitor is 2(2-((2-chloro-6-fluorophenyl)amino)5-methylphenyl)acetic acid (COX 189, registration number 220991-20-8), and its derivatives, as disclosed in, for example, WO 99/11605, WO 01/23346 and WO 02/20090, the disclosures of each of which are incorporated by reference herein in their entirety. The structure of the preferred embodiment parent COX-2 selective inhibitor, 2(2-((2-chloro-6-fluorophenyl)amino)5-methylphenyl)acetic acid (COX 189), is shown below:

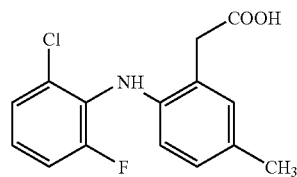

In other preferred embodiments of the invention, the nitrosated derivatives of the compounds of Formula (I) are the nitrosated derivatives of the COX-2 selective inhibitor, 2(2-((2-chloro-6-fluorophenyl)amino)5-methylphenyl)acetic acid (COX 189). In even more preferred embodiments of the invention the nitrosated derivatives of the COX-2 selective inhibitor, COX-189, are compounds of Formula (II), (III), (IV), (V), (VI), (VII), (VIII) and (IX) and pharmaceutically acceptable salts thereof:

wherein the compound of Formula (II), 2-(2-(nitroxy)ethylthio)ethyl 2(2-((2-chloro-6-fluorophenyl)amino)5-methylphenyl)acetate, is:

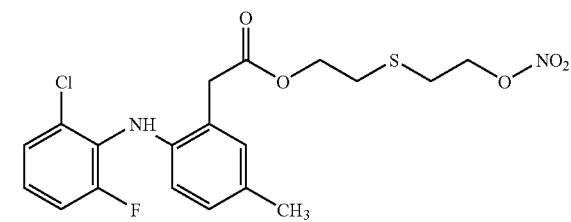

(II)

wherein the compound of Formula (III), 2-(2-(nitroxy)ethoxy)ethyl 2(2-((2-chloro-6-fluorophenyl)amino)5-methylphenyl)acetate, is:

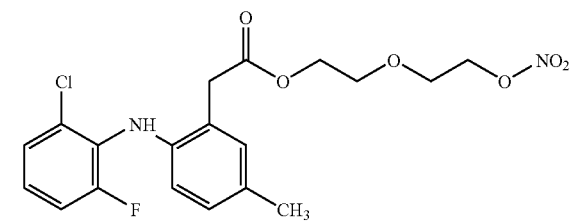

(III)

wherein the compound of Formula (IV), 3-((nitroxy)methylphenyl)2(2-((2-chloro-6-fluorophenyl)amino)5-methylphenyl)acetate, is:

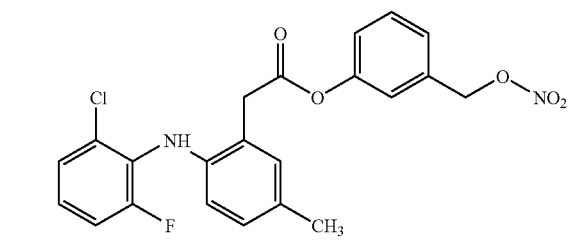

(IV)

wherein the compound of Formula (V), 2,3-bis(nitroxy) propyl 2(2-((2-chloro-6-fluorophenyl)amino)5-methylphenyl)acetate, is:

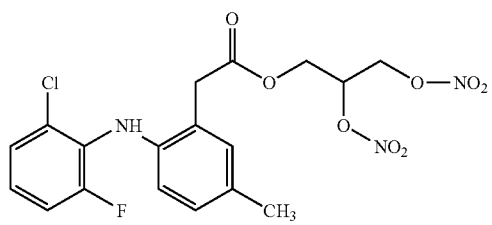

(V)

wherein the compound of Formula (VI), 6-(nitroxy)-4,8-dioxabicyclo(3.3.0)oct-2-yl 2-(2-((2-chloro-6-fluorophenyl)amino)5-methylphenyl)acetate, is:

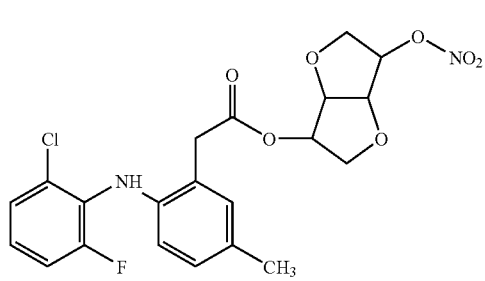

(VI)

wherein the compound of Formula (VII), 2-((2-(nitroxy)ethyl)sulfonyl)ethyl 2(2-((2-chloro-6-fluorophenyl)amino)5-methylphenyl)acetate, is:

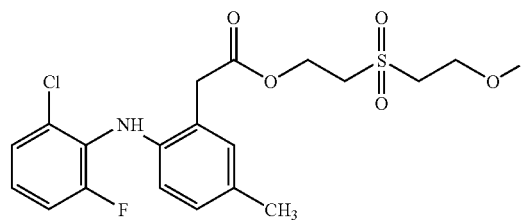

(VII)

wherein the compound of Formula (VIII), 2-(4-(2-nitrooxyl)ethyl)piperazinyl)-2-oxoethyl 2-(2-((2-chloro-6-fluorophenyl)amino)5-methylphenyl)acetate, is:

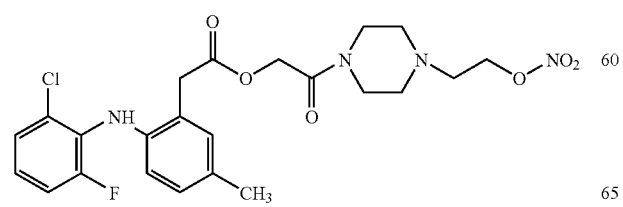

(VIII)

wherein the compound of Formula (IX), 2,3-bis(nitroxy)-4-(2-(2-((2-chloro-6-fluorophenyl)amino)5-methylphenyl)acetyloxy)butyl 2-(2-((2-chloro-6-fluorophenyl)amino)5-methylphenyl)acetate, is:

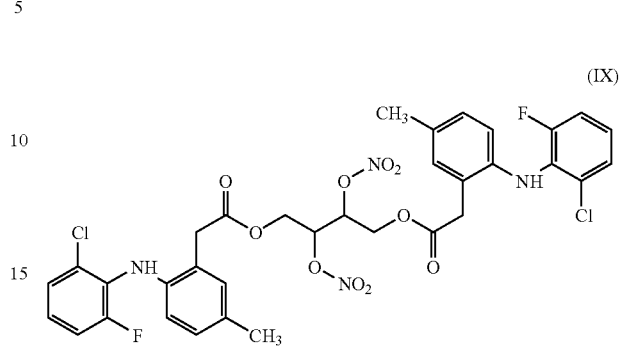

(IX)

Another aspect of the invention describes the metabolites of the compounds of Formula (II), (III), (IV), (V), (VI), (VII), (VIII), (IX) and pharmaceutically acceptable salts thereof. These metabolites, include but are not limited to, the non-nitrosated derivatives of the compounds of Formula (II), (III), (IV), (V), (VI), (VII), (VIII), (IX) and pharmaceutically acceptable salts thereof, such as, for example the compounds of Formulas (X), (XI), (XII), (XIII), (XIV), (XV), (XVI) and (XVII):

wherein the compound of Formula (X), 2-(2-(hydroxyethylthio)ethyl 2(2-((2-chloro-6-fluorophenyl)amino)5-methylphenyl)acetate, is:

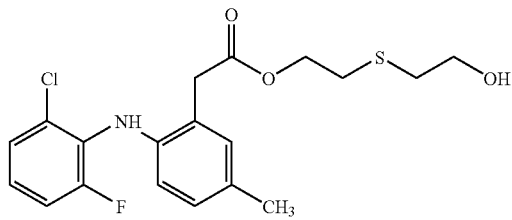

(X)

wherein the compound of Formula (XI), 2-(2-(hydroxyethoxy)ethyl 2(2-((2-chloro-6-fluorophenyl)amino)5-methylphenyl)acetate, is:

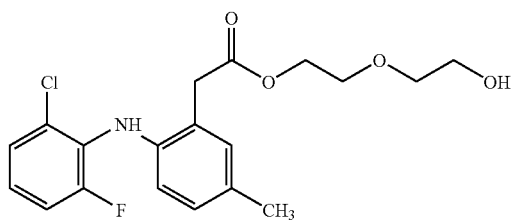

(XI)

wherein the compound of Formula (XII), 3-(hydroxymethylphenyl)2(2-((2-chloro-6-fluorophenyl)amino)5-methylphenyl)acetate, is:

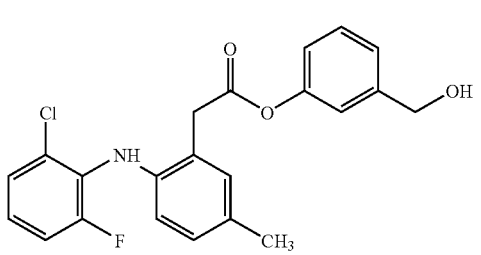

(XII)

wherein the compound of Formula (XIII), 2,3-dihydroxypropyl 2(2-((2-chloro-6-fluorophenyl)amino)5-methylphenyl)acetate, is:

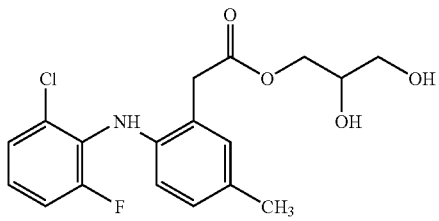

(XIII)

wherein the compound of Formula (XIV), 6-hydroxy-4,8-dioxabicyclo(3.3.0)oct-2-yl 2(2-((2-chloro-6-fluorophenyl)amino)5-methylphenyl)acetate, is:

(XIV)

wherein the compound of Formula (XV), 2-((2-hydroxyethyl)sulfonyl)ethyl 2(2-((2-chloro-6-fluorophenyl)amino)5-methylphenyl)acetate, is:

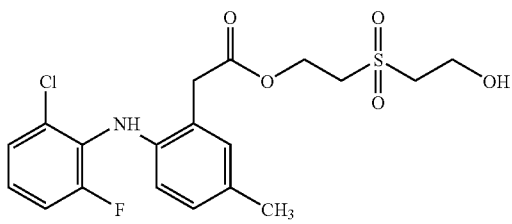

(XV)

wherein the compound of Formula (XVI), 2-(4-(2-hydroxyethyl)piperazinyl)-2-oxoethyl 2-(2-((2-chloro-6-fluorophenyl)amino)5-methylphenyl)acetate, is:

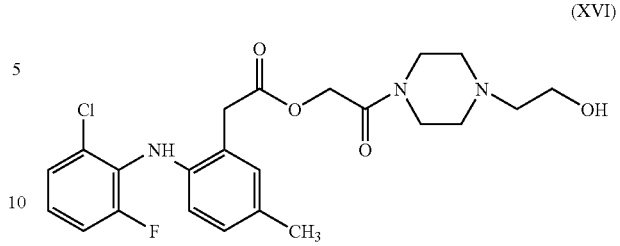

(XVI)

wherein the compound of Formula (XVII), 4-(2-(2-((2-chloro-6-fluorophenyl)amino)5-methylphenyl)acetoxy)-2,3-dihydroxybutyl-2-(2-((2-chloro-6-fluorophenyl)amino)5-methylphenyl)acetyloxy)butyl acetate, is:

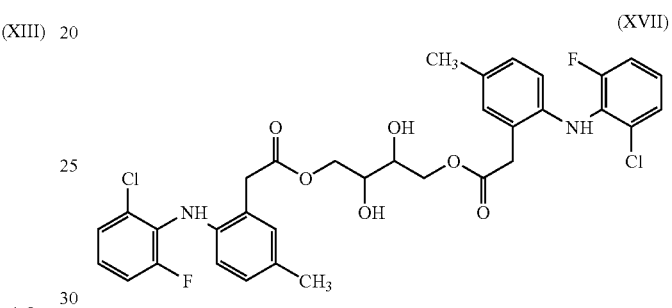

(XVII)

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The invention includes within its scope all such isomers and mixtures thereof.

Another aspect of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application for the preparation of the compounds of this invention. The chemical reactions are described by, for example, Smith and March, *March's Advanced Organic Chemistry, Reactions, Mechanisms and Structure*, Fifth Edition, John Wiley & Sons, New York (2001) and by Larock, *Comprehensive Organic Transformations*, VCH Publishers, Inc. (1989). The compounds of the invention can be synthesized in a number of ways well known to one skilled in the art of organic synthesis. The compounds can be synthesized using the methods described herein, together with synthetic methods known in the art of synthetic organic chemistry, or by convention modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials. Methods for the preparation of the compounds, include, but are not limited to, those described below. All references cited herein are hereby incorporated herein by reference in their entirety.

Nitroso compounds of Formula (I), wherein $R_4$, $R_5$, $R_6$, $R_7$, $R_8$, and $R_9$ are as defined herein, and an O-nitrosylated ester is representative of the "X—K" group as defined herein may be prepared as described below. An appropriate acid of the compound of Formula (I) (i.e., wherein "X—K" is an hydroxyl group) is converted into the ester by reaction with an appropriate monoprotected diol. Preferred methods for the preparation of esters are coupling the acid and the monoprotected diol by treatment with a dehydration agent such as dicyclohexylcarbodiimide (DCC). Alternatively, the acid may first be converted into an alkali metal salt such as the sodium, potassium or lithium salt, and reacted with an alkyl halide that also contains a protected hydroxyl group in a polar solvent such as DMF to produce the ester. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite or nitrosium tetrafluoroborate in a suitable anhydrous solvent such as dichlormethane, THF, DMF or acetonitrile produces the compound of Formula (I).

Nitroso compounds of Formula (I), wherein $R_4$, $R_5$, $R_6$, $R_7$, $R_8$, and $R_9$ are as defined herein, and a S-nitrosylated ester is representative of the "X—K" group as defined herein may be prepared as described below. An appropriate acid of the compound of Formula (I) (i.e., wherein "X—K" is a hydroxyl group) is converted into the ester by reaction with an appropriate protected thiol containing alcohol. Preferred methods for the preparation of esters are coupling the appropriate acid and protected thiol-containing alcohol to produce the ester by treatment with a dehydration agent such as DCC. Alternatively, the acid may first be converted into an alkali metal salt such as the sodium, potassium or lithium salt, which is then reacted with an alkyl halide which also contains a protected thiol group in a polar solvent such as DMF to produce the ester. Preferred protecting groups for the thiol moiety are as a thioester such as thioacetate or thiobenzoate, as a disulfide, as a thiocarbamate such as N-methoxymethyl thiocarbamate, or as a thioether such as paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile produces the compound of Formula (I). Alternatively, a stoichiometric quantity of sodium nitrite in an aqueous acid mixture produces the compound of Formula (I).

The synthesis of the parent COX-2 inhibitors (i.e. non-nitrosated and/or non-nitrosylated COX-2 inhibitors) are disclosed in, for example, WO 99/11605, WO 01/23346 and WO 02/20090, the disclosures of each of which are incorporated by reference herein in their entirety. The parent COX-2 selective inhibitor can be nitrosated and/or nitrosylated through one or more sites such as oxygen, sulfur and/or nitrogen using the methods described in the examples herein and using conventional methods known to one skilled in the art. For example, known methods for nitrosating and nitrosylating compounds are described in U.S. Pat. Nos. 5,380,758 and 5,703,073; 6,297,260, WO 97/27749; WO 98/19672; WO 01/45703; and Oae et al, Org. Prep. Proc. Int., 15(3):165-198 (1983), the disclosures of each of which are incorporated by reference herein in their entirety. The methods of nitrosating and/or nitrosylating the compounds in these references can be applied by one skilled in the art to produce any of the nitrosated and/or nitrosylated compounds of Formula (I) described herein. The nitrosated and/or nitrosylated compounds of Formula (I), (II), (III), (IV), (V), (VI), (VII), (VIII) and (IX) (i.e. nitrosated and/or nitrosylated COX-2 selective inhibitors) of the invention donate, transfer or release a biologically active form of nitrogen monoxide (nitric oxide).

The nitrosated compounds of Formula (II), (III), (IV), (V), (VI), (VII), (VIII) or (IX) can be synthesized using the methods for nitrosating non-steroidal antiinflammatory compounds (NSAIDs) disclosed in, for example, WO 94/03421, WO 94/04484, WO 94/12463, WO 95/09831, WO 95/30641, WO 01/00563 and WO 01/04082, WO 01/10814 and in U.S. Application No. 60/418,353; the disclosures of each of which are incorporated by reference herein in their entirety.

The compounds of the invention include the parent COX-2 inhibitors, including those described herein, which have been nitrosated and/or nitrosylated through one or more sites such as oxygen (hydroxyl condensation), sulfur (sulfhydryl condensation) and/or nitrogen. The nitrosated and/or nitrosylated COX-2 inhibitors of the invention donate, transfer or release a biologically active form of nitrogen monoxide (i.e., nitric oxide).

Nitrogen monoxide can exist in three forms: NO− (nitroxyl), NO. (uncharged nitric oxide) and NO+ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO+) does not react with $O_2$ or $O_2^-$ species, and functionalities capable of transferring and/or releasing NO+ and NO− are also resistant to decomposition in the presence of many redox metals. Consequently, administration of charged NO equivalents (positive and/or negative) is a more effective means of delivering a biologically active NO to the desired site of action.

Compounds contemplated for use in the invention (e.g., COX-2 selective inhibitor, that can be optionally nitrosated and/or nitrosylated, are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO.) and charged nitrogen monoxide species, preferably charged nitrogen monoxide species, such as nitrosonium ion (NO+) and nitroxyl ion (NO−). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z,3E)-4-ethyl-2-(hydroxyimino)-6-methyl-5-nitro-3-heptenyl)-3-pyridinecarboxamide (FR 146801), nitrosoamines, furoxans as well as substrates for the endogenous enzymes which synthesize nitric oxide. NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino)diazen-1-ium-1,2-diolate (spermine NONOate or "SPER/NO") and sodium(Z)-1-(N,N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof; S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3): 165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:
(i) HS(C($R_e$)($R_f$))$_m$SNO;
(ii) ONS(C($R_e$)($R_f$))$_m$$R_e$; or
(iii) $H_2N$—CH($CO_2H$)—($CH_2$)$_m$—C(O)NH—CH($CH_2$SNO)—C(O)NH—$CH_2$—$CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring. a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, —T—Q—, or —(C($R_g$)($R_h$))$_k$—T—Q or $R_e$ and $R_f$ taken together are an oxo, a methanthial, a heterocyclic ring, a cycloalkyl group, an oxime, a hydrazone or a bridged cycloalkyl group; Q is —NO or —$NO_2$; and T is independently a covalent bond, a carbonyl, an oxygen, —S(O)$_o$— or —N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —$CH_2$—C(T—Q)($R_g$)($R_h$), or —($N_2O_2$—)$^−$.$M^+$, wherein $M^+$ is an organic or inorganic cation; with the proviso that when $R_i$ is —$CH_2$—C(T—Q)($R_g$)($R_h$) or —($N_2O_2$—).$M^+$; then "—T—Q" can be a hydrogen, an alkyl group, an alkoxyalkyl group, an aminoalkyl group, a hydroxy group or an aryl group; and $R_g$ and $R_h$ at each occurrence are independently $R_e$;

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluroroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N-polypeptides (the term "polypeptide" includes proteins and polyamino acids that do not possess an ascertained biological function, and derivatives thereof); ON—O— or ON—N-amino acids (including natural and synthetic amino acids and their stereoisomers and racemic mixtures); ON—O— or ON—N-sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds.

Another group of NO adducts for use in the invention include nitrates that donate, transfer or release nitric oxide, such as compounds comprising at least one $O_2N$—O—, $O_2N$—N— or $O_2N$—S— group. Preferred among these compounds are $O_2N$—O—, $O_2N$—N— or $O_2N$—S-polypeptides (the term "polypeptide" includes proteins and also polyamino acids that do not possess an ascertained biological function, and derivatives thereof); $O_2N$—O—, $O_2N$—N— or $O_2N$—S-amino acids (including natural and synthetic amino acids and their stereoisomers and racemic mixtures); $O_2N$—O—, $O_2N$—N— or $O_2N$—S— sugars; $O_2N$—O—, $O_2N$—N— or $O_2N$—S— modified and unmodified oligonucleotides (comprising at least 5 nucleotides, preferably 5-200 nucleotides); $O_2N$—O—, $O_2N$—N— or $O_2N$—S— straight or branched, saturated or unsaturated, aliphatic or aromatic, substituted or unsubstituted hydrocarbons; and $O_2N$—O—, $O_2N$—N— or $O_2N$—S— heterocyclic compounds. Preferred examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1''}R^{2''}N$—N(O—$M^+$)—NO, where $R^{1''}$ and $R^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M^+$ is an organic or inorganic cation, such as, for example, an alkyl substituted ammonium cation or a Group I metal cation.

The invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524-526 (1987); Ignarro et al, *Proc. Natl. Acad. Sci. USA*, 84:9265-9269 (1987)).

The invention is also based on the discovery that compounds and compositions of the invention may be used in conjunction with other therapeutic agents for co-therapies, partially or completely, in place of other conventional antiinflammatory compounds, such as, for example, together with steroids, NSAIDs, 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG-CoA inhibitors, $H_2$ receptor antagonists, antineoplastic agents, antiplatelet agents, thrombin inhibitors, thromboxane inhibitors, decongestants, diuretics, sedating or non-sedating anti-histamines, inducible nitric oxide synthase inhibitors, opiods, analgesics, *Helicobacter pylori* inhibitors, proton pump inhibitors, isoprostane inhibitors, and mixtures of two or more thereof.

Leukotriene $A_4$ ($LTA_4$) hydrolase inhibitors refer to compounds that selectively inhibit leukotriene $A_4$ hydrolase with an $IC_{50}$ of less than about 10 μM, and preferably with an $IC_{50}$ of less than about 1 μM. Suitable $LTA_4$ hydrolase inhibitors include, but are not limited to, RP-64966, (S,S)-3-amino-4-(4-benzyloxyphenyl)-2-hydroxybutyric acid benzyl ester, N-(2(R)-(cyclohexylmethyl)-3-(hydroxycarbamoyl)propionyl)-L-alanine, 7-(4-(4-ureidobenzyl)phenyl) heptanoic acid and 3 (3-(1E,3E-tetradecadienyl)-2-oxiranyl)benzoic acid lithium salt, and mixtures of two or more thereof.

Suitable $LTB_4$ receptor antagonists include, but are not limited to, ebselen, linazolast, ontazolast; WAY 121006; Bay-x-1005; B1-RM-270; CGS-25019C; ETH-615; MAFP; TMK-688; T-0757; LY 213024, LY 210073, LY 223982, LY 233469, LY 255283, LY 264086, LY 292728 and LY 293111; ONO-LB457, ONO-4057, and ONO-LB-448, S-2474, calcitrol; PF 10042; Pfizer 105696; RP 66153; SC-53228, SC-41930, SC-50605, SC-51146 and SC-53228; SB-201146 and SB-209247; SKF-104493; SM 15178; TMK-688; BPC 15, and mixtures of two or more thereof. The preferred $LTB_4$ receptor antagonists are calcitrol, ebselen, Bay-x-1005, CGS-25019C, ETH-615, LY-293111, ONO-4057 and TMK-688, and mixtures of two or more thereof.

Suitable 5-LO inhibitors include, but are not limited to, A-76745, 78773 and ABT761; Bay-x-1005; CMI-392; E-3040; EF-40; F-1322; ML-3000; PF-5901; R-840; rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast, and mixtures of two or more thereof. Suitable 5-LO inhibitors are also described more fully in WO 97/29776, the disclosure of which is incorporated herein by reference in its entirety.

Suitable 5-HT agonists, include, but are not limited to, rizatriptan, sumatriptan, naratriptan, zolmitroptan, eleptriptan, almotriptan, ergot alkaloids. ALX 1323, Merck L 741604 SB 220453 and LAS 31416. Suitable 5-HT agonists are described more fully in WO 0025779, and in WO 00/48583. 5-HT agonists refers to a compound that is an agonist to any 5-HT receptor, including but not limited to, $5\text{-HT}_1$ agonists, $5\text{-HT}_{1B}$ agonists and $5\text{-HT}_{1D}$ agonists, and the like.

Suitable steroids, include, but are not limited to, budesonide, dexamethasone, corticosterone, prednisolone, and the like. Suitable steroids are described more fully in the literature, such as in the Merck Index on CD-ROM, 13$^{th}$ Edition.

Suitable HMG CoA inhibitors, include, but are not limited to, reductase and synthase inhibitors, such as, for example, squalene synthetase inhibitors, benzodiazepine squalene synthase inhibitors, squalene epoxidase inhibitors, acyl-coenzyme A, bile acid sequestrants, cholesterol absorption inhibitors, and the like. Suitable HMG CoA inhibitors include simvastatin, pravastatin, lovastatin, mevastatin, fluvastatin, atorvastatin, cerivastatin, and the like, and are described more fully in U.S. Pat. No. 6,245,797 and WO 99/20110, the disclosures of which are incorporated herein by reference in their entirety.

Suitable NSAIDs, include, but are not limited to, acetaminophen, aspirin, diclofenac, ibuprofen, ketoprofen, naproxen, indomethacin, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S. Pat. Nos. 6,057,347 and 6,297,260 assigned to NitroMed Inc., the disclosures of which are incorporated herein by reference in their entirety.

Suitable H$_2$ receptor anatgonists, include, but are not limited to, cimetidine, roxatidine, rantidine and the like. Suitable H$_2$ receptor antagonists are described more fully in the literature, such as in Goodman and Gilman, The Pharmacological Basis of Therapeutics (9th Edition), McGraw-Hill, 1995, Pgs. 901-915; the Merck Index on CD-ROM, 13$^{th}$ Edition; and in WO 00/28988 assigned to NitroMed Inc., the disclosures of which are incorporated herein by reference in their entirety.

Suitable antineoplastic agents, include but are not limited to, 5-FU-fibrinogen, acanthifolic acid, aminothiadiazole, altretamine, anaxirone, aclarubicin and the like. Suitable antineoplastic agents are also described in U.S. Pat. No. 6,025,353 and WO 00/38730, the disclosures of which are incorporated herein by reference in their entirety.

Suitable antiplatelet agents, include but are not limited to, aspirin, ticlopidine, dipyridamole, clopidogrel, glycoprotein IIb/IIIa receptor antagonists, and the like. Suitable antineoplastic agents are also described in WO 99/45913, the disclosure of which is incorporated herein by reference in its entirety. In a preferred embodiment of the invention, the antiplatelet agent is aspirin, more preferably, low-dose aspirin (i.e. 75 mg-100 mg/day).

Suitable thrombin inhibitors, include but are not limited to, N'-((1-(aminoiminomethyl)-4-piperidinyl)methyl)-N-(3,3-diphenylpropinyl)-L-proline amide),3-(2-phenylethylamino)-6-methyl-1-(2-amino-6-methyl-5-methylene-carboxamidomethylpyridinyl)-2-pyrazinone, 3-(2-phenethylamino)-6-methyl-1-(2-amino-6-methyl-5-methylenecarboxamidomethylpyridinyl)-2-pyridinone, and the like. Suitable thrombin inhibitors are also described in WO 00/18352, the disclosure of which is incorporated herein by reference in its entirety.

Suitable thromboxane inhibitors, include but are not limited to thromboxane synthase inhibitors, thromboxane receptor antagonists, and the like. Suitable thromboxane inhibitors, are also described in WO 01/87343, the disclosure of which is incorporated herein by reference in its entirety.

Suitable decongestants include, but are not limited to, phenylephrine, phenylpropanolamine, pseudophedrine, oxymetazoline, ephinephrine, naphazoline, xylometazoline, propylhexedrine, levo-desoxyephedrine, and the like.

Suitable antitussives include, but are not limited to, codeine, hydrocodone, caramiphen, carbetapentane, dextramethorphan, and the like.

Suitable proton pump inhibitors, include, but are not limited to, omeprazole, esomeprazole, lansoprazole, rabeprazole, pantoprazole, and the like. Suitable proton pump inhibitors are described more fully in the literature, such as in Goodman and Gilman, The Pharmacological Basis of Therapeutics (9th Edition), McGraw-Hill, 1995, Pgs. 901-915; the Merck Index on CD-ROM, 13$^{th}$ Edition; and in WO 00/50037 assigned to NitroMed Inc., the disclosures of which are incorporated herein by reference in their entirety.

The compounds and compositions of the invention, may also be used in combination therapies with opioids and other analgesics, including, but not limited to, narcotic analgesics, Mu receptor antagonists, Kappa receptor antagonists, non-narcotic (i.e. non-addictive) analgesics, monoamine uptake inhibitors, adenosine regulating agents, cannabinoid derivatives, neurokinin 1 receptor antagonists, Substance P antagonists, neurokinin-1 receptor antagonists, sodium channel blockers, N-methyl-D-aspartate receptor antagonists, and mixtures of two or more thereof. Preferred combination therapies would be with morphine, meperidine, codeine, pentazocine, buprenorphine, butorphanol, dezocine, meptazinol, hydrocodone, oxycodone, methadone, Tramadol ((+) enantiomer), DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol ((−) enantiomer), GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, CP-99,994, and mixtures of two or more thereof.

The compounds and compositions of the invention can also be used in combination with inducible nitric oxide synthase (iNOS) inhibitors. Suitable iNOS inhibitors are disclosed in U.S. Pat. Nos. 5,132,453 and 5,273,875, and in WO 97/38977 and WO 99/18960, the disclosures of each of which are incorporated by reference herein in their entirety.

The invention is also based on the discovery that the administration of a therapeutically effective amount of the compounds and compositions described herein is effective for treating inflammation, pain (both chronic and acute), and fever, such as, for example, analgesic in the treatment of pain, including, but not limited to headaches, migraines, postoperative pain, dental pain, muscular pain, and pain resulting from cancer; as an antipyretic for the treatment of fever, including but not limited to, rheumatic fever, symptoms associated with influenza or other viral infections, common cold, low back and neck pain, dysmenorrhea, headache, toothache, sprains, strains, myositis, neuralgia, synovitis; arthritis, including but not limited to rheumatoid arthritis, degenerative joint disease (osteoarthritis), spondyloarthropathies, gouty arthritis, systemic lupus erythematosus and juvenile arthritis. For example, the patient can be administered a therapeutically effective amount of least one nitrosated and/or nitrosylated derivative of the COX-2 selective inhibitor of the invention. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, including but not limited to, steroids, nonsterodal antiinflammatory compounds (NSAID), 5-lipoxygenase (5-LO) inhibitors, leukotriene B$_4$ (LTB$_4$) receptor antagonists, leukotriene A$_4$ (LTA$_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods for decreasing and/or preventing gastrointestinal disorders and improving the gastrointestinal properties of the COX-2 selective inhibitor by administering to the patient in need thereof a therapeutically effective amount of the compounds and/or compositions described herein. Such gastrointestinal disorders refer to any disease or disorder of the upper gastrointestinal tract (e.g., esophagus, the stomach, the duodenum, jejunum) including, for example, inflammatory bowel disease, Crohn's disease, gastritis, irritable bowel syndrome, ulcerative colitis, peptic ulcers, stress ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. For example, the patient can be administered a therapeutically effective amount of at least one nitrosated and/or nitrosylated derivative of the COX-2 selective inhibitor of the invention. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, including but not limited to, including but not limited to, steroids, nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Yet another embodiment of the invention provides methods for facilitating wound healing (such as, for example, ulcer healing, bone healing including osteoporosis) by administering to the patient in need thereof a therapeutically effective amount of the compounds and/or compositions described herein. Wound refers to, and includes, any lesion that is characterized by loss of tissue, and, includes, but are not limited to, ulcers, cuts, burns, bone fractures, orthopedic procedure, would infliction, and the like. Ulcers refers to lesions of the upper gastrointestinal tract lining that are characterized by loss of tissue, and, include, but are not limited to, gastric ulcers, duodenal ulcers, gastritis, and the like. For example, the patient can be administered a therapeutically effective amount of at least one nitrosated and/or nitrosylated derivative of the COX-2 selective inhibitor of the invention. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, and, optionally, at least one nitric oxide donor. The compounds can be administered separately or in the form of a composition.

Another embodiment of the invention provides methods to decrease or reverse renal and other toxicities (such as, for example, kidney toxicity, respiratory toxicity) by administering to a patient in need thereof a therapeutically effective amount of the compounds and/or compositions described herein. For example, the patient can be administered a therapeutically effective amount of at least one nitrosated and/or nitrosylated COX-2 selective inhibitor of the invention. In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, and at least one therapeutic agent, and, optionally, at least one nitric oxide donor. The compounds can be administered separately or in the form of a composition.

Another embodiment of the invention provides methods to treat or prevent disorders resulting from elevated levels of COX-2 by administering to a patient in need thereof a therapeutically effective amount of the compounds and/or compositions described herein. For example, the patient can be administered a therapeutically effective amount of at least one COX-2 selective inhibitor, that is optionally nitrosated and/or nitrosylated, of the invention. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and at least one therapeutic agent, including but not limited to, steroids, a nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Disorders resulting from elevated levels of COX-2 (e.g., COX-2 mediated disorders) include, but are not limited to, for example, angiogenisis, arthritis, asthma, bronchitis, menstrual cramps, premature labor, tendinitis, bursitis; skin-related conditions, such as, for example, psoriasis, eczema, surface wounds, burns and dermatitis; post-operative inflammation including from ophthalmic surgery, such as, for example, cataract surgery and refractive surgery, and the like; treatment of neoplasia, such as, for example, brain cancer, bone cancer, epithelial cell-derived neoplasia (epithelial carcinoma), such as, for example, basal cell carcinoma, adenocarcinoma, gastrointestinal cancer, such as, for example, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body, benign and cancerous tumors, growths, polyps, adenomatous polyps, including, but not limited to, familial adenomatous polyposis, fibrosis resulting from radiation therapy, and the like; treatment of inflammatory processes in diseases, such as, for example, vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like; treatment of ophthalmic diseases and disorders, such as, for example, retinitis, retinopathies, uveitis, ocular photophobia, acute injury to the eye tissue, glaucoma, inflammation of the eye and elevation of intraocular pressure and the like; treatment of pulmonary inflammation, such as, for example, those associated with viral infections and cystic fibrosis, and the like; treatment of central nervous system disorders, such as, for example, cortical dementias including Alzheimer's disease, vascular dementia, multi-infarct dementia, pre-senile dementia, alcoholic dementia, senile dementia, and central nervous system damage resulting from stroke, ischemia and trauma, and the like; treatment of allergic rhinitis, respiratory distress syndrome, endotoxin shock syndrome, atherosclerosis; treatment of inflammations and/or microbial infections including, for example, inflammations and/or infections of the eyes, ears, nose, throat, and/or skin; treatment and/or prevention of cardiovascular disorders, such as, for example, coronary artery disease, aneurysm, arteriosclerosis, atherosclerosis, including, but not limited to, cardiac transplant atherosclerosis, myocardial infarction, hypertension, ischemia, embolism, stroke, thrombosis, venous thrombosis, thromboembolism, thrombotic occlusion and reclusion, restenosis, angina, unstable angina, shock, heart failure, coronary plaque inflammation, bacterial-induced inflammation, such as, for example, *Chlamydia*-induced inflammation, viral induced inflammation, inflammation associated with surgical procedures, such as, for example, vascular grafting, coronary artery bypass surgery, revascularization procedures, such as, for example, angioplasty, stent placement, endarterectomy, vascular procedures involving arteries, veins, capillaries, and the like; treatment and/or prevention of urinary and/or urological disorders, such as, for example, incontinence and the like; treatment and/or prevention of endothelial dysfunctions, such as, for example, diseases accompanying these dysfunctions, endothelial damage from hypercholesterolemia, endothelial damage from hypoxia, endothelial damage from mechanical and chemical noxae, especially during and after drug, and mechanical reopening of stenosed vessels, for example, following percutaneous transluminal angiography (PTA) and percuntaneous transluminal coronary angiography (PTCA), endothelial damage in postinfarction phase, endothelium-mediated reocculusion following bypass surgery, blood supply distrubances in peripheral arteries, as well as, cardiovascular diseases, and the like; disorders treated by the preservation of organs and tissues, such as, for example, for organ transplants, and the like; disorders treated by the inhibition and/or prevention of activation, adhesion and infiltration of neutrophils at the site of inflammation; and disorders treated by the inhibition and/or prevention of platelet aggregation. The compounds and compositions of the invention can also be used as a pre-anesthetic medication in emergency operations to reduce the danger of aspiration of acidic gastric contents.

Another embodiment of the invention provides methods for improving the cardiovascular profile of COX-2 selective inhibitors by administering to a patient in need thereof a therapeutically effective amount of the compounds and/or compositions described herein. For example, the patient can be administered a therapeutically effective amount of at least one nitrosated and/or nitrosylated COX-2 selective inhibitor of the invention. In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, at least one of 3-hydroxy-3-methylglutaryl coenzyme A (HMG-CoA) inhibitors, antiplatelet agents, thrombin inhibitors, thromboxane inhibitors, and, optionally, at least one nitric oxide donor. The compounds can be administered separately or in the form of a composition.

When administered separately, the COX-2 selective inhibitor, that is optionally nitrosated and/or nitrosylated, can be administered about the same time as part of the overall treatment regimen i.e., as a combination therapy. "About the same time" includes administering the COX-2 selective inhibitor, that is optionally nitrosated and/or nitrosylated, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one COX-2 selective inhibitor and/or at least one nitrosated and/or nitrosylated COX-2 selective inhibitor and/or at least one nitric oxide donor and/or therapeutic agent, they can also be used in combination with one or more additional compounds which are known to be effective against the specific disease state targeted for treatment. The nitric oxide donors, therapeutic agents and/or other additional compounds can be administered simultaneously with, subsequently to, or prior to administration of the COX-2 selective inhibitor and/or nitrosated and/or nitrosylated COX-2 selective inhibitor.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

The preferred methods of administration of the COX-2 selective inhibitors and compositions for the treatment of gastrointestinal disorders are orally, bucally or by inhalation. The preferred methods of administration for the treatment of inflammation and microbial infections are orally, bucally, topically, transdermally or by inhalation.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given COX-2 selective inhibitor of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the COX-2 selective inhibitor. The usual daily doses of the COX-2 selective inhibitors are about 0.001 mg to about 140 mg/kg of body weight per day, preferably 0.005 mg to 30 mg/kg per day, or alternatively about 0.5 mg to about 7 g per patient per day. For example, inflammations may be effectively treated by the administration of from about 0.01 mg to 50 mg of the compound per kilogram of body weight per day, or alternatively about 0.5 mg to about 3.5 g per patient per day. The compounds may be administered on a regimen of up to 6 times per day, preferably 1 to 4 times per day, and most preferably once per day. Effective doses may be extrapolated from dose-response curves derived from in vitro or animal model test systems and are in the same ranges or less than as described for the commercially available compounds in the Physician's Desk Reference, supra.

The invention also provides pharmaceutical kits comprising one or more containers filled with one or more of the ingredients of the pharmaceutical compounds and/or compositions of the invention, including, at least, one or more of the novel COX-2 selective inhibitors, that is optionally nitrosated and/or nitrosylated, and one or more of the NO donors described herein. Associated with such kits can be additional therapeutic agents or compositions (e.g., steroids, NSAIDs, 5-lipoxygenase (5-LO) inhibitors, leukotriene $B_4$ ($LTB_4$) receptor antagonists and leukotriene $A_4$ ($LTA_4$) hydrolase inhibitors, 5-HT agonists, HMG-CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like), devices for administering the compositions, and notices in the form prescribed by a governmental agency regulating the manufacture, use or sale of pharmaceuticals or biological products which reflects approval by the agency of manufacture, use or sale for humans.

What is claimed is:

1. 2,3-bis(nitroxy)-4-(2-(2-((2-chloro-6-fluorophenyl)amino)5-methylphenyl)acetyloxy)butyl 2-(2-((2-chloro-6-fluorophenyl)amino)5-methylphenyl)acetate, or a pharmaceutically acceptable salt thereof.

2. A composition comprising the compound of claim 1 and a pharmaceutically acceptable carrier.

3. The composition of claim 2, further comprising at least one therapeutic agent.

4. The composition of claim 3, wherein the therapeutic agent is a steroid, a nonsteroidal antiinflammatory compound, a 5-lipoxygenase (5-LO) inhibitor, a leukotriene $B_4$ receptor antagonist, a leukotriene $A_4$ hydrolase inhibitor, a 5-HT agonist, a HMG CoA inhibitor, a $H_2$ antagonist, an antineoplastic agent, an antiplatelet agent, a thrombin inhibitor, a thromboxane inhibitor, a decongestant, a diuretic, a sedating or non-sedating anti-histamine, an inducible nitric oxide synthase inhibitor, an opioid, an analgesic, a *Helicobacter pylori* inhibitor, a proton pump inhibitor, an isoprostane inhibitor, or a mixture of two or more thereof.

5. A composition comprising the compound of claim 1 or a pharmaceutically acceptable salt thereof, and at least one compound that donates, transfers or releases nitric oxide, or induces the production of endogenous nitric oxide or endothelium-derived relaxing factor, or is a substrate for nitric oxide synthase.

6. The composition of claim 5 further comprising a pharmaceutically acceptable carrier.

7. The composition of claim 5, wherein the compound that donates, transfers, or releases nitric oxide, or induces the production of endogenous nitric oxide or endothelium-derived relaxing factor or is a substrate for nitric oxide synthase is an S-nitrosothiol.

8. The composition of claim 7, wherein the S-nitrosothiol is S-nitroso-N-acetylcysteine, S-nitroso-captopril, S-nitroso- N-acetylpenicillamine, S-nitroso-homocysteine, S-nitroso-cysteine, S-nitroso-glutathione, or S-nitroso-cysteinyl-glycine.

9. The composition of claim 7, wherein the S-nitrosothiol is:
   (i) $HS(C(R_e)(R_f))_m SNO$;
   (ii) $ONS(C(R_e)(R_f))_m R_e$; or
   (iii) $H_2NCH(CO_2H)$—$(CH_2)_m$—$C(O)NH$—$CH(CH_2SNO)$—$C(O)NH$—$CH_2CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, —T—Q—, or $(C(R_g)(R_h))_k$—T—Q or $R_e$ and $R_f$ taken together are an oxo, a methanthial, a heterocyclic ring, a cycloalkyl group, an oxime, a hydrazone or a bridged cycloalkyl group; Q is —NO or —NO$_2$; and T is independently a covalent bond, a carbonyl, an oxygen, —S(O)$_o$— or —N(R$_a$)R$_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —CH$_2$—C(T—Q)(R$_g$)(R$_h$), or —(N$_2$O$_2$—)$^-$.M$^+$, wherein M$^+$ is an organic or inorganic cation; with the proviso that when $R_i$ is —CH$_2$—C(T—Q)(R$_g$)(R$_h$) or —(N$_2$O$_2$—).M$^+$; then "—T—Q" can be a hydrogen, an alkyl group, an alkoxyalkyl group, an aminoalkyl group, a hydroxy group or an aryl group; and $R_g$ and $R_h$ at each occurrence are independently $R_e$.

10. The composition of claim 5, wherein the compound that donates, transfers, or releases nitric oxide, or induces the production of endogenous nitric oxide or endothelium-derived relaxing factor, or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, nitrosated L-homoarginine, nitrosylated L-homoarginine), citrulline, ornithine, glutamine, lysine, an arginase inhibitor or a nitric oxide mediator.

11. The composition of claim 5, wherein the compound that donates, transfers, or releases nitric oxide, or induces the production of endogenous nitric oxide or endothelium-derived relaxing factor, or is a substrate for nitric oxide synthase is:
   (i) a compound that comprises at least one ON—O— or ON—N— group;
   (ii) a compound that comprises at least one O$_2$N—O—, O$_2$N—N— or O$_2$N—S— or group;
   (iii) a N-oxo-N-nitrosoamine having the formula: R$^{1''}$R$^{2''}$N—N(O—M$^+$)—NO, wherein R$^{1''}$ and R$^{2''}$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M$^+$ is an organic or inorganic cation.

12. The composition of claim 11, wherein the compound comprising at least one ON—O— or ON—N— group is an ON—O-polypeptide, an ON—N-polypeptide, an ON—O-amino acid, an ON—N-amino acid, an ON—O-sugar, an ON—N-sugar, an ON—O-oligonucleotide, an ON—N-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, an ON—O-heterocyclic compound or an ON—N-heterocyclic compound.

13. The composition of claim 11, wherein compound comprising at least one O$_2$N—O—, O$_2$N—N— or O$_2$N—S— group is an O$_2$N—O-polypeptide, an O$_2$N—N-polypeptide, an O$_2$N—S-polypeptide, an O$_2$N—O-amino acid, O$_2$N—N-amino acid, O$_2$N—S-amino acid, an O$_2$N—O-sugar, an O$_2$N—N-sugar, O$_2$N—S-sugar, an O$_2$N—O-oligonucleotide, an O$_2$N—N-oligonucleotide, an O$_2$N—S-oligonucleotide, a straight or branched, saturated or unsaturated, aliphatic or aromatic, substituted or unsubstituted O$_2$N—O-hydrocarbon, a straight or branched, saturated or unsaturated, aliphatic or aromatic, substituted or unsubstituted O$_2$N—N-hydrocarbon, a straight or branched, saturated or unsaturated, aliphatic or aromatic, substituted or unsubstituted O$_2$N—S-hydrocarbon, an O$_2$N—O-heterocyclic compound, an O$_2$N—N-heterocyclic compound or an O$_2$N—S-heterocyclic compound.

14. The composition of claim 5, further comprising at least one therapeutic agent.

15. The composition of claim 14, wherein the therapeutic agent is a steroid, a nonsteroidal antiinflammatory compound, a 5-lipoxygenase (5-LO) inhibitor, a leukotriene B$_4$ receptor antagonist, a leukotriene A$_4$ hydrolase inhibitor, a 5-HT agonist, a HMG CoA inhibitor, a H$_2$ antagonist, an antineoplastic agent, an antiplatelet agent, a thrombin inhibitor, a thromboxane inhibitor, a decongestant, a diuretic, a sedating or non-sedating anti-histamine, an inducible nitric oxide synthase inhibitor, an opioid, an analgesic, a *Helicobacter pylori* inhibitor, a proton pump inhibitor, an isoprostane inhibitor, or a mixture of two or more thereof.

16. A kit comprising at least one compound of claim 1 or a pharmaceutically acceptable salt thereof.

17. The kit of claim 16, further comprising at least one compound that donates, transfers or releases nitric oxide, induces the production of endogenous nitric oxide or endothelium-derived relaxing factor, or is a substrate for nitric oxide synthase or at least one therapeutic agent.

18. The kit of claim 17, wherein the at least one compound that donates, transfers or releases nitric oxide, induces the production of endogenous nitric oxide or endothelium-derived relaxing factor, or is a substrate for nitric oxide synthase or the at least one therapeutic agent are in the form of separate components in the kit or are in the form of a composition in the kit.

19. A kit comprising the composition of claim 3, 5 or 14.

* * * * *